United States Patent [19]

Conrow et al.

[11] 4,337,249

[45] Jun. 29, 1982

[54] MODULATORS OF THE COMPLEMENT SYSTEM

[75] Inventors: Ransom B. Conrow, Pearl River; Seymour Bernstein, New City, both of N.Y.

[73] Assignee: American Cyanamid Company, Stamford, Conn.

[21] Appl. No.: 289,641

[22] Filed: Aug. 3, 1981

[51] Int. Cl.$^3$ .................. A61K 31/70; C07H 13/12
[52] U.S. Cl. .................................. 424/180; 424/14; 424/16; 424/56; 536/53; 536/118; 536/122
[58] Field of Search ............... 424/180; 536/118, 122, 536/53

[56] References Cited

U.S. PATENT DOCUMENTS 4,098,995  7/1978  Nair et al. .................... 536/118
4,221,907  9/1980  Nair et al. .................... 536/118

*Primary Examiner*—Johnnie R. Brown
*Attorney, Agent, or Firm*—Anne M. Rosenblum

[57] ABSTRACT

N-(4-O-α-D-glucopyranosyl-β-D-glucopyranosyl)-3,4-dihydroxycinnamamide, nonakis (H-sulfate) (nona-ester), nona-alkali metal or alkaline earth metal-salts, useful as modulators of the complement system, the intermediates thereof and the process of making such salts and intermediates.

15 Claims, No Drawings

MODULATORS OF THE COMPLEMENT SYSTEM

BACKGROUND OF THE INVENTION

1. Field of Invention

The present invention relates to novel N-(4-O-α-D-glucopyranosyl-β-D-glucopyranosyl)-3,4-dihydroxycinnamamide, nonakis (H-sulfate) (nonaester), nonaalkali metal or alkaline earth metal-salts, to their use as modulators of the complement system of warm-blooded animals, to the intermediates thereof and to the process for the preparation of such intermediates and end products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973): Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis [6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,983 or South African Pat. No. 727, 923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem 47:547 (1969); J. Immunol. 104: 279 (1970); J. Immunol. 106: 241 (1971); J. Immunol. 111: 1061 (1973); Biochem. Biophys. Acts 317: 539 (1973); Life Sci. 13: 351 (1973); J. Immunol. 113: 584 (1974); Immunology 26: 819 (1974); J. Med. Chem. 17: 1160 (1974); Biochem.

Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci 66: 1367 (1977); Chem. Pharm. Bull. 25: 1202 (1977); Biochem. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979): Biochem. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972): 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both *in vitro* and *in vivo,* as judged by the reduction in total hemolytic complement activity, Pathol. Biol. 25: 33; 25 (2): 105; 25 (3): 179 (1977).

SUMMARY OF THE INVENTION

The instant invention relates to new compounds N-(4-O-α-D-glucopyranosyl-β-D-glucopyranosyl)-3,4-dihydroxycinnamamide, nonakis (H-sulfate) (nonaester), nonalkali metal cation or alkaline earth metal cation salts that modulate the complement system, thereby modulating complement activity in body fluids. Moreover, this invention involves a method of modulating the complement systems in a body fluid which comprises subjecting body fluid complement to the action of an effective complement inhibiting amount of the above-identified compounds. This invention further concerns a method of inhibiting the complement system in a warm-blooded animal which comprises administering to said animal a therapeutically effective complement inhibiting amount of the above-identified compounds.

This invention also deals with the novel precursors N-(4-O-α-D-glucopyranosyl-β-D-glucopyranosyl)-3,4-dihydroxycinnamamide and N-(4-O-α-D-glucopyranosyl-β-D-glucopyranosyl)-3,4-dihydroxycinnamamide, nonakis (H-sulfate) (nonaester) nonatrialkylamine salts [where A is trialkyl (C₁–C₃)] that act as intermediates in preparing the above-described complement modulating compounds of this invention.

DETAILED DESCRIPTION OF THE INVENTION

In accordance with the present invention, there are provided novel compounds represented by the following generic Formula I:

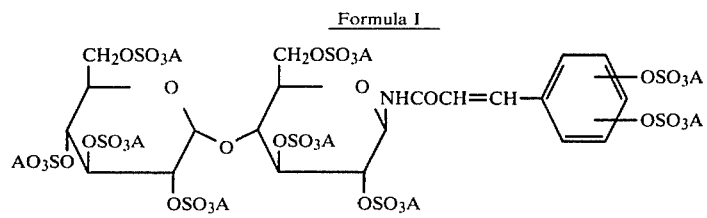

Formula I wherein A is selected from the group consisting of alkali metal cations and alkaline earth metal cations. A particularly preferred compound of this invention which is of major interest as a modulator of the complement system is N-(4-O-α-D-glucopyranosyl-β-D-glucopyranosyl)-3,4-dihydroxycinnamamide, nonakis (H-sulfate) (nonaester), nonasodium salt.

This invention further deals with a method of modulating the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention also concerns a method of inhibiting the complement system in a warm-blooded animal which comprises administering to said warm-blooded animal a therapeutically effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums.

In addition, this invention is concerned with the precursors of the complement-modulating compounds, shown by the following Formula II:

Formula II

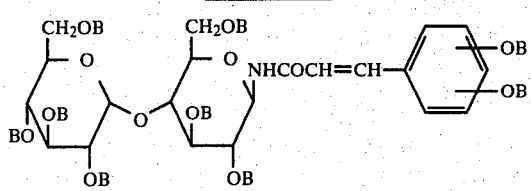

wherein B is selected from the group consisting of hydrogen and —SO₃A where A is trialkyl (C₁–C₃). The instant invention is specifically concerned with the compounds N-(4-O-α-D-glucopyranosyl-β-D-glucopyranosyl)-3,4-dihydroxycinnamamide, nonakis (H-sulfate) (nonaester) nonatrialkylamine salts [wherein B is —SO₃A and A is trialkyl (C₁–C₃)]. This compound is an intermediate for the preparation of the previously described alkali metal and alkaline earth metal cation salts which are modulators of the complement system. This invention further deals with the preferred compound N-(4-O-α-D-glucopyranosyl-β-D-glucopyranosyl)-3,4-dihydroxycinnamamide [wherein B is hydrogen] which is of special interest as a precursor to the intermediate nonatrialkylamine salts.

The compounds of this invention may be prepared according to the following flowchart.

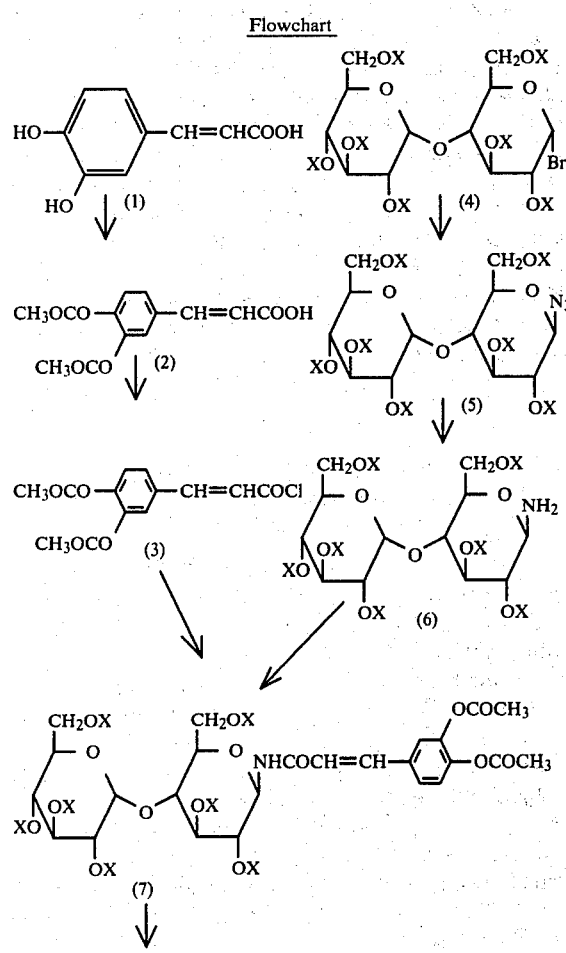

-continued
Flowchart

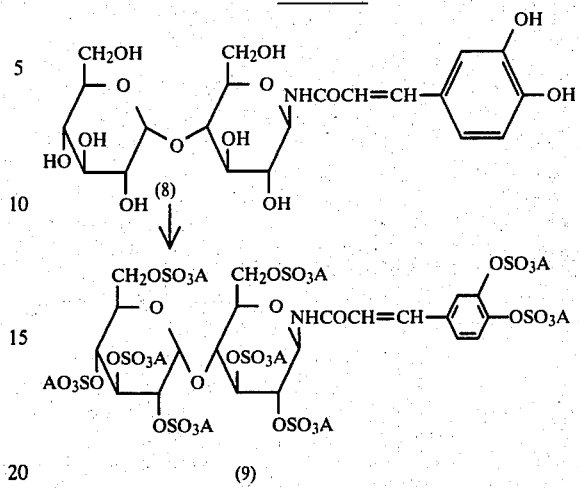

In accordance with the above flowchart, 3,4-dihydroxycinnamic acid (1) is reacted with acetic anhydride in pyridine for 18–30 hours and then extracted with organic solvents, giving 3,4-dihydroxycinnamic acid, diacetate (2) which is further converted to the 3,4-dihydroxycinnamic acid chloride (3) by treatment with thionyl chloride in dimethylformamide at −20° to −18° C. for 30–90 minutes.

4-O-α-D-glucopyranosyl-β-D-glucopyranosyl bromide, heptaacetate (4) is reacted with sodium azide in dimethylsulfoxide at 55°–65° C. for 10–30 minutes followed by extraction in organic solvents, giving 4-O-α-D-glucopyranosyl-β-D-glucopyranosylazide, heptaacetate (6). The azide is hydrogenated at room temperature under pressure in dioxane-triethylamine solution using 10% palladium on carbon catalyst. The product is crystallized from dioxane-ethanol to provide 4-O-α-D-glucopyranosyl-β-D-glucopyranosylamine, heptaacetate (heptaester).

A solution of 3,4-dihydroxycinnamic acid chloride (3) in dimethylformamide at −20° to −15° C. is reacted with 4-O-α-D-glucopyranosyl-β-D-glucopyranosylamine heptaacetate (6) in pyridine at −15° to −5° C. for 30 minutes, then at −5° to +20° C. for 1–2 hours, then extracted with organic solvents, giving N-(4-O-α-D-glucopyranosyl-β-D-glucopyranosyl)-3,4-dihydroxycinnamamide, nonaacetate (nonaester) (7). This nonaacetate (7) is then converted to N-(4-O-α-D-glucopyranosyl-β-D-glucopyranosyl)-3,4-dihydroxycinnamamide (8) by reaction in methanol, triethylamine and water, under an inert atmosphere at ambient temperature for 20–30 hours followed by refluxing for 2–6 hours and extraction in organic solvents. The free sugar derivative (8) is then reacted with triethylamine sulfur trioxide in N,N-dimethylacetamide under an inert atmosphere at 50°–70° C. for 15–20 hours followed by treatment with an alkali or alkaline earth metal acetate in water giving the products (9), where A is the alkali or alkaline earth metal cation.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also it should be appreciated that when typical reaction conditions (e.g., temperatures, mole ratios, reaction times) have been given, the conditions which are both above and below these specified ranges can also be used, though generally less conveniently.

The salts of the present invention include the alkali metal cations and the alkaline earth metal cations. Typical alkali metal cations are, for example, sodium and potassium. Typical alkaline earth metal cations are, for example, calcium and magnesium.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

3,4-Dihydroxycinnamic acid, diacetate

A mixture of 18.02 g of 3,4-dihydroxycinnamic acid, 60 ml of pyridine and 30 ml of acetic anhydride is stirred until solution is complete and then allowed to stand overnight. The solution is poured into water, the mixture extracted with dichloromethane and the extract washed with water, dried and concentrated in vacuo to a small volume. The concentrate is diluted with toluene to give a brown crystalline precipitate which is recrystallized from ethyl acetate, giving 10.45 g of the desired compound as a tan powder, m.p. 202°–207° C.

EXAMPLE 2

4-O-α-D-Glucopyranosyl-β-D-glucopyranosylazide, heptaacetate

To a solution of 26 g of sodium azide in 600 ml of dimethylsulfoxide at 62° C. is added 140 g of 4-Oα-D-glucopyranosyl-β-D-glucopyranosyl bromide, heptaacetate. The solution is stirred at 58°–63° C. for 15 minutes then poured into ice-water and the solid is collected, washed with water and dissolved in dichloromethane. This solution is dried, concentrated in vacuo to an oil and crystallized twice from 60% aqueous ethanol, giving 90 g of the desired compound as colorless crystals, m.p. 93°–100° C.

EXAMPLE 3

4-O-α-D-Glucopyranosyl-β-D-glucopyranosylamine, heptaacetate (heptaester)

Hydrogen is bubbled through a briskly stirred solution of 110 g of 4-O-α-D-glucopyranosyl-β-D-glucopyranosylazide, heptaacetate in one liter of dioxane, containing 1% triethylamine and 14 g of 10% palladium on carbon catalyst, at 25°–40° C. until thin-layer chromatography (30% acetone, toluene on silica gel) indicates that the reduction is complete. The mixture is filtered through celite, concentrated in vacuo to about 350 ml and added to 1–8 liters of hot, absolute ethanol. This mixture is allowed to crystallize at 5° C. and the solid is recrystallized twice from acetonitrile containing 1% triethylamine, giving 68.9 g of the desired compound as colorless crystals, m.p. 195°–198° C.

EXAMPLE 4

N-(4-O-α-D-Glucopyranosyl-β-D-glucopyranosyl)-3,4-dihydroxycinnamamide, nonaacetate (nonaester)

To a solution of 20.1 g of 3,4-dihydroxycinnamic acid diacetate in 300 ml of dimethylformamide at −23° C. in a nitrogen atmosphere, is added 5.81 ml of thionyl chloride. The solution is stirred at −20° to −18° C. for one hour, then 12.2 ml of pyridine are added followed by 48.3 g of 4-O-β-D-glucopyranosyl-β-D-glucopyranosylamine, heptaacetate (heptaester). This mixture is stirred at −15° to −5° C. for 30 minutes, then at −5° to 20° C. for 1.5 hours. The solution is poured into 2 liters of cold water and the solid is collected, washed with water and dissolved in dichloromethane. This solution is dried and evaporated to an amber glass which is crystallized four times from toluene and once from ethanol, giving the desired compound as colorless crystals, m.p. 156°–162° C.

EXAMPLE 5

N-(4-O-α-D-Glucopyranosyl-β-D-glucopyranosyl)-3,4-dihydroxycinnamamide

A solution of 25.57 g of N-(4-O-α-D-glucopyranosyl-β-D-glucopyranosyl)-3,4-dihydroxycinnamamide, nonaacetate (nonaester) in a mixture of 273 ml of methanol, 136 ml of triethylamine and 91 ml of water, under nitrogen, is allowed to stand for 24 hours, then is refluxed, under nitrogen, for 4 hours. The solution is evaporated in vacuo to a small volume and the residue is co-evaporated several times with ethanol until all water is removed. The product is dissolved in 75 ml of methanol, diluted with 250 ml of ethanol and filtered. The filtrate is evaporated to a gum which is dissolved in 100 ml of methanol and added to 750 ml of ether with vigorous stirring. The solid is collected and dried at 78° C., giving the desired intermediate as a yellow powder.

EXAMPLE 6

N-(4-O-α-D-Glucopyranosyl-β-D-glucopyranosyl)-3,4-dihydroxycinnamamide, nonakis (H-sulfate), (nonaester), nonasodium salt A mixture of 10.1 g of N-(4-O-α-D-glucopyranosyl-β-D-glucopyranosyl)-3,4-dihydroxycinnamamide, 10.0 g of 4 A° molecular sieves and 65.25 g of triethylamine sulfur trioxide in 200 ml of N,N-dimethylacetamide is stirred and heated at 56°–65° C., in an inert atmosphere, for 18 hours. The mixture is filtered through celite and poured into 2 liters of acetone, giving a gum. The supernatant is decanted and the gum dissolved in a solution of 16.4 g of anhydrous sodium acetate in 100 ml of water. This solution is poured into 2.5 liters of absolute ethanol with vigorous stirring. The white precipitate is collected, washed with ethanol, then ether and dried in vacuo at 78° C., giving 24.1 g of the desired product as an off-white powder.

EXAMPLE 7

Preparation of Compressed Tablet

| Ingredient | mg/Tablet |
| --- | --- |
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 8

Preparation of Compressed Tablet—Sustained Action

| Ingredient | mg/Tablet |
| --- | --- |
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 9

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 10

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 11

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

Preparation of Injectable Solution

| Ingredient | % W/V |
| --- | --- |
| Active Compound | 0.05–5 |
| Benzyl Alcohol NF | 0.9 |
| Water for Injection | 100.0 |

EXAMPLE 14

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 15

Preparation of Intra-Articular Product

| Ingredient | Amount |
| --- | --- |
| Active Compound | 2–20 mg |
| NaCl (physiological saline) | 0.9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 16

Preparation of Injectable Depo Suspension

| Ingredient | % W/V |
| --- | --- |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 17

Preparation of Dental Paste

| Ingredient | % W/W |
| --- | --- |
| Active Compound | 0.05–5 |
| Zinc Oxide | 15 |
| Polyethylene Glycol 4000 USP | 50 |
| Distilled Water qs | 100 |

EXAMPLE 18

Preparation of Dental Ointment

| Ingredient | % W/W |
|---|---|
| Active Compound | 0.05-5 |
| Petrolatum, White USP qs | 100 |

EXAMPLE 19

Preparation of Dental Cream

| Ingredient | % W/W |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 20

Preparation of Topical Cream

| Ingredient | % W/W |
|---|---|
| Active Compound | 0.05-5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 21

Preparation of Topical Ointment

| Ingredient | % W/W |
|---|---|
| Active Compound | 0.05-5 |
| Cholesterol | 3 |
| Stearyl Alcohol | 3 |
| White Wax | 8 |
| Petrolatum, White USP qs | 100 |

EXAMPLE 22

Preparation of Spray Lotion (Non-aerosol)

| Ingredient | % W/W |
|---|---|
| Active Compound | 0.05-5 |
| Isopropyl Myristate | 20 |
| Alcohol (Denatured) qs | 100 |

EXAMPLE 23

Preparation of Buccal Tablet

| Ingredient | mg/Tablet |
|---|---|
| Active Ingredient | 3.25 |
| 6 X Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 24

Preparation of Lozenge

| Ingredient | g/Lozenge |
|---|---|
| Active Ingredient | 0.0140 |
| Kompact ® Sugar (Sucrest Co.) | 0.7138 |
| 6 X Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅜" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of compounds of this invention has been demonstrated by the following identified tests: (i) Test Code 026 (C1 inhibitor) This test measures the ability of activated human C1 to destroy fluid phase human C2 in the presence of C4 and appropriate dilutions of the test compound. An active inhibitor protects $C_2$ from C1 and $C_4$; (ii) Cap 50 Test Here, appropriate amounts of the test compound are added to a pool of guinea pig serum in vitro, after which the undiluted serum capillary tube assay of U.S. Pat. No. 3,876,376 is run. The concentration of compound inhibiting 50% is reported; and (iii) Guinea Pig Intraperitoneal Test (GPIP)—Guinea pigs weighing about 300 g are dosed intraperitoneally (i.p.) with 200 mg kg of the test compound dissolved in saline and adjusted to pH 7-8. Approximately 0.4 ml blood samples, taken by orbital sinus puncture 2 hours and 6 hours after injections, are collected directly into centrifuge tubes; 5 ml blood samples, taken by decapitation 24 hours after injection, are collected directly into beakers. The samples are allowed to clot, centrifuged, and the resultant sera are assayed for complement activity using the capillary complement assay. Percent inhibition are calculated by comparison with simultaneous controls. The results of the GPIP appear in Table I together with results of Test Code 026 and Cap 50. Table I shows that the principal compound of the invention possesses highly significant in vitro and in vivo complement inhibiting activity in warm-blooded animals.

TABLE I

| | Biological Activities | | | | |
|---|---|---|---|---|---|
| | In vitro Activity | | In vivo Activity (Guinea pig % Inhibition) | | |
| | Cl 026* | Cap | Intraperitoneal Time (Hours) | | |
| Compound | Wells | 50 | 2 | 6 | 24 |
| N-(4-O-α-D-Glucopyranosyl-β-D-glucopyranosyl)-3,4-dihydroxy-cinnamamide, nonakis (H-sulfate) (nonaester), nonasodium salt | 8 (9) | 304 | 63 | 17 | 2 |

*Tests identified by code herein.
**Activity in wells, a serial dilution assay; higher well number indicates higher activity. The serial dilutions are two-fold.

We claim:

1. A compound selected from those of the formula:

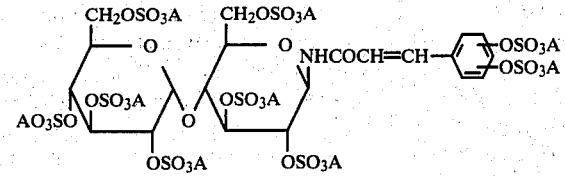

wherein A is selected from the group consisting of alkali metal cations and alkaline earth metal cations.

2. The compound according to claim 1, N-(4-O-α-D-glucopyranosyl-β-D-glucopyranosyl)-3,4-dihydroxycinnamamide, nonakis (H-sulfate), (nonaester), nonasodium salt.

3. A compound selected from those of the formula:

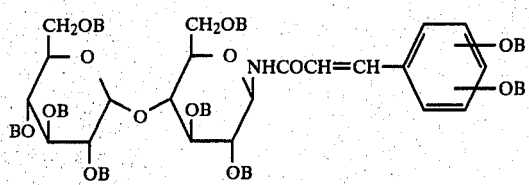

wherein B is selected from the group consisting of hydrogen and —$SO_3A$ where A is trialkyl ($C_1$–$C_3$).

4. The compound according to claim 3, N-(4-O-α-D-glucopyranosyl-β-D-glucopyranosyl)-3,4-dihydroxycinnamamide.

5. The compound according to claim 3, N-(4-O-α-D-glucopyranosyl-β-D-glucopyranosyl)-3,4-dihydroxycinnamamide, nonakis (H-sulfate), (nonaester), nonatriethylamine salt.

6. A method of modulating the complement system in a body fluid which comprises subjecting said body fluid to the action of an effective complement modulating amount of a pharmaceutically acceptable compound selected from those of the formula:

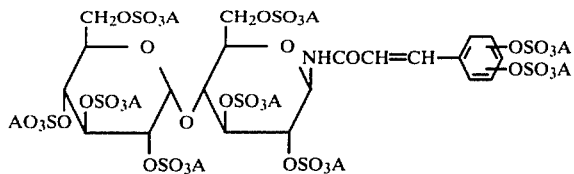

wherein A is selected from the group consisting of alkali metal cations and alkaline earth metal cations.

7. The method according to claim 6, wherein the body fluid is blood serum.

8. A method of modulating the complement system in a warm-blooded animal which comprises administering to said warm-blooded animal a therapeutically effective complement modulating amount of a pharmaceutically acceptable compound selected from those of the formula:

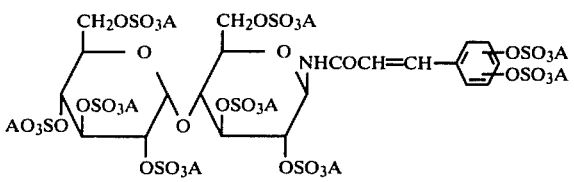

wherein A is selected from the group consisting of alkali metal cations and alkaline earth metal cations.

9. The method according to claim 6 or 8, wherein the compound is N-(4-O-α-D-glucopyranosyl-β-D-glucopyranosyl)-3,4-dihydroxycinnamamide, nonakis (H-sulfate), (nonaester), nonasodium salt.

10. The method according to claim 8, wherein the compound is adminstered internally.

11. The method according to claim 8, wherein the compound is administered topically.

12. The method according to claim 8, wherein the compound is administered periodontally in the oral cavity.

13. The method according to claim 8, wherein the compound is administered intra-articularly.

14. The method according to claim 8, wherein the compound is administered parenterally.

15. A method for producing compounds of the formula:

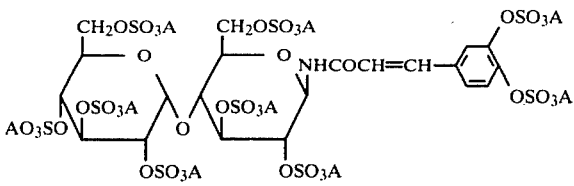

wherein A is selected from the group consisting of alkali metal cations and alkaline earth metal cations which comprises reacting 3,4-dihydroxycinnamic acid with acetic anhydride in pyridine for 18-30 hours, in organic solvents, giving 3,4-dihydroxycinnamic acid, diacetate, then converting to 3,4-dihydroxycinnamic acid chloride by treating with thionyl chloride in dimethylformamide at $-20°$ to $-18°$ C. for 30-90 minutes; reacting 4-O-α-D-glucopyranosyl-β-D-glucopyranosyl bromide, heptaacetate with sodium azide in dimethylsulfoxide at $55°-65°$ C. for 10-30 minutes, extracting in organic solvents, giving 4-O-α-D-glucopyranosyl-β-D-glucopyranosylazide, heptaacetate, then catalytically reducing, giving 4-Oα-D-glucopyranosyl-β-D-glucopyranosylamine, heptaacetate (heptaester); reacting a solution of the 3,4-dihydroxycinnamic acid chloride in dimethylformamide at $-20°$ to $-15°$ C. with a solution of the 4-O-α-D-glucopyranosyl-β-D-glucopyranosylamine, heptaacetate in pyridine at $-15°$ to $-5°$ C. for 20-40 minutes, then at $-5°$ to 20° C. for 1-2 hours followed by extracting with organic solvents, giving N-(4-O-α-D-glucopyranosyl-β-D-glucopyranosyl)-3,4-dihydroxycinnamamide, nonaacetate (nonaester), then converting to N-(4-O-α-D-glucopyranosyl-β-D-glucopyranosyl)-3,4-dihydroxycinnamamide by reacting in a mixture of methanol, triethylamine and water, under an inert atmosphere for 20-30 hours followed by heating at reflux for 2-6 hours and extracting in organic solvents, reacting this derivative with triethylamine sulfur trioxide in N,N-dimethylacetamide under an inert atmosphere at $50°-70°$ C. for 15-20 hours, and then treating with an alkali metal or alkaline earth metal acetate in water.

* * * * *